(12) United States Patent
Dewey

(10) Patent No.: US 11,344,429 B2
(45) Date of Patent: May 31, 2022

(54) SPINAL IMPLANT SYSTEM AND METHOD

(71) Applicant: WARSAW ORTHOPEDIC INC., Warsaw, IN (US)

(72) Inventor: Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 151 days.

(21) Appl. No.: 16/867,216

(22) Filed: May 5, 2020

(65) Prior Publication Data
US 2021/0346170 A1 Nov. 11, 2021

(51) Int. Cl.
*A61F 2/44* (2006.01)
*A61F 2/30* (2006.01)

(52) U.S. Cl.
CPC .... *A61F 2/4425* (2013.01); *A61F 2002/3055* (2013.01); *A61F 2002/30421* (2013.01); *A61F 2002/30523* (2013.01); *A61F 2002/30538* (2013.01); *A61F 2002/443* (2013.01)

(58) Field of Classification Search
CPC ........ A61F 2/44; A61F 2/4425; A61F 2/4455; A61F 2/447; A61F 2/46; A61F 2002/30421; A61F 2002/30523; A61F 2002/30538; A61F 2002/3055; A61F 2002/443
USPC ............................................ 623/17.11–17.16
See application file for complete search history.

(56) References Cited

U.S. PATENT DOCUMENTS

| | | | |
|---|---|---|---|
| 7,850,733 B2 | 12/2010 | Baynham et al. | |
| 9,848,993 B2 | 12/2017 | Moskowitz et al. | |
| 10,137,006 B2* | 11/2018 | Dewey ............... | A61F 2/4611 623/17.16 |
| 10,188,527 B2 | 1/2019 | Rogers et al. | |
| 2014/0343678 A1* | 11/2014 | Suddaby ............... | A61F 2/4611 623/17.16 |
| 2016/0331542 A1* | 11/2016 | Faulhaber ............... | A61F 2/447 623/17.16 |
| 2018/0206999 A1 | 7/2018 | Suddaby | |
| 2019/0110900 A1 | 4/2019 | Suddaby | |

FOREIGN PATENT DOCUMENTS

WO 2019022976 A1 1/2019

* cited by examiner

*Primary Examiner* — Jessica Weiss
(74) *Attorney, Agent, or Firm* — Sorell, Lenna & Schmidt, LLP

(57) ABSTRACT

A spinal implant includes a first member extending along a first axis between opposite first and second ends. The first end includes a first part. A rack is coupled to the first member. A second member extends along a second axis between opposite first and second ends. A gear is coupled to the second member such that the gear engages the rack. An actuator includes a second part that engages the first part such that rotation of the actuator relative to the members translates the rack relative to the first member along the first axis to move the implant between a first orientation in which the second longitudinal axis extends parallel to the first longitudinal axis and a second orientation in which the second longitudinal axis extends at an acute angle relative to the first longitudinal axis. Systems and methods are disclosed.

20 Claims, 3 Drawing Sheets

SPINAL IMPLANT SYSTEM AND METHOD

TECHNICAL FIELD

The present disclosure generally relates to medical devices for the treatment of musculoskeletal disorders, and more particularly to a spinal construct configured for disposal with spaced vertebrae and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior technologies.

SUMMARY

In one embodiment, a spinal implant is provided. The spinal implant includes a first member extending along a first longitudinal axis between opposite first and second ends. The first end comprises a first mating part. A rack is coupled to the first member. A second member extends along a second longitudinal axis between opposite first and second ends. A gear is coupled to the second end of the second member such that the gear engages the rack. An actuator comprises a second mating part that engages the first mating part such that rotation of the actuator relative to the members translates the rack relative to the first member along the first longitudinal axis to move the implant between a first orientation in which the second longitudinal axis extends parallel to the first longitudinal axis and a second orientation in which the second longitudinal axis extends at an acute angle relative to the first longitudinal axis.

In one embodiment, a spinal implant is provided. The spinal implant includes a first member having a first vertebral engaging surface. The first member extends along a first longitudinal axis between opposite first and second ends. The first end comprises a first mating part. A rack is coupled to the first member. A second member includes a second vertebral engaging surface. The second member extends along a second longitudinal axis between opposite first and second ends. A gear is coupled to the second end of the second member. An actuator comprises a second mating part that engages the first mating part. A distance between the vertebral engaging surfaces defines a height of the implant. Rotation of the actuator relative to the members translates the rack relative to the first member along the first longitudinal axis such that the gear rotates relative to the rack to increase the height of the implant.

In one embodiment, a spinal implant is provided. The spinal implant includes a first member extending along a first longitudinal axis between opposite first and second ends. The first end comprises a first mating part. A rack is coupled to the first member. A second member extends along a second longitudinal axis between opposite first and second ends. A first pin extends into the first end of the first member and the first end of the second member such that the second member is pivotable relative to the first member about the first pin. A gear is coupled to the second end of the second member such that the gear engages the rack. An actuator is rotatably coupled to the rack. The actuator comprises a second mating part that engages the first mating part such that rotation of the actuator relative to the members translates the rack relative to the first member along the first longitudinal axis to move the implant between a first orientation in which the second longitudinal axis extends parallel to the first longitudinal axis and a second orientation in which the second longitudinal axis extends at an acute angle relative to the first longitudinal axis. The first member comprises a first vertebral engaging surface and the second member comprises an opposite second vertebral engaging surface. A distance between the vertebral engaging surfaces defines a maximum height of the implant. The maximum height of the implant is greater when the implant is in the second orientation than when the implant is in the first orientation. The rack includes spaced apart arms having a plurality of spaced apart first teeth and the gear includes spaced apart legs having a plurality of second teeth. The second teeth engage the first teeth as the implant moves between the first and second orientations. The second end of the second member comprises spaced apart extensions. The gear is positioned between the extensions such that a second pin extends through the extensions and the gear and the gear is pivotable relative to the extensions about the second pin. The gear rotates relative to the second member as the implant moves between the first and second orientations.

BRIEF DESCRIPTION OF THE DRAWINGS

The present disclosure will become more readily apparent from the specific description accompanied by the following drawings, in which.

DETAILED DESCRIPTION

Figure 1:
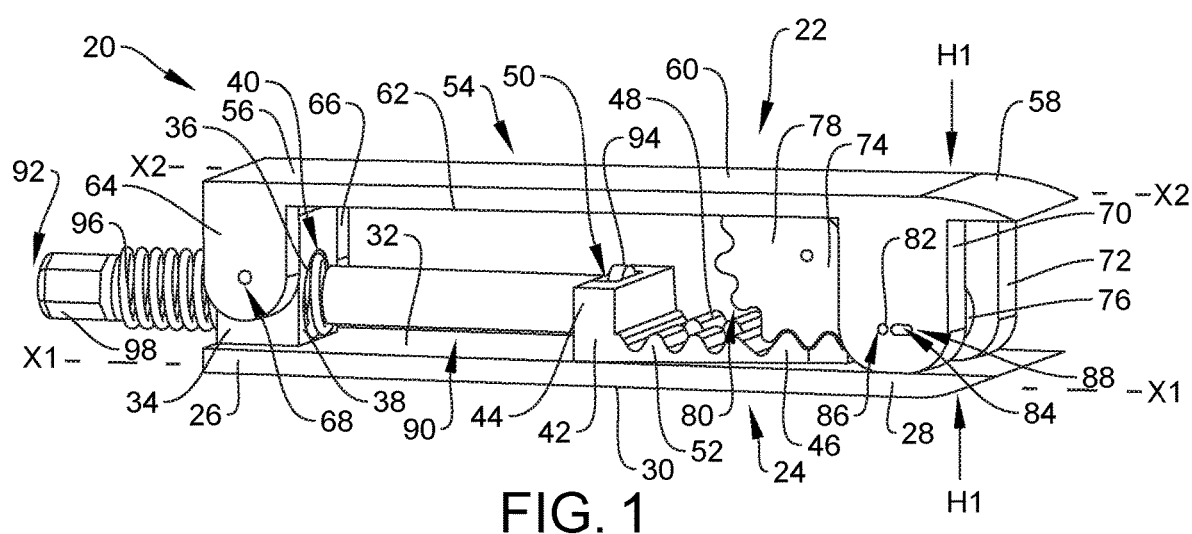
FIG. 1 is a perspective view of a spinal implant in accordance with the principles of the present disclosure.

The exemplary embodiments of a surgical system and related methods of use disclosed are discussed in terms of medical devices for the treatment of musculoskeletal disorders and more particularly, in terms of a spinal implant system that includes an expandable interbody implant configured for disposal with spaced vertebrae and a method for treating a spine.

In some embodiments, the expandable interbody implant is an expanding interbody cage based on a rack and pinion mechanism. In some embodiments, the expandable interbody implant is an expanding interbody device based on a threaded bar pushing a rack which rotates a cam and expands the device. In some embodiments, reduced zero-height force is needed to expand require the device.

In some embodiments, the expandable interbody implant is an expanding interbody device based on a rack that drives a spur gear to expand the interbody device. In some embodiments, the rack is pushed forward as a threaded bar is turned such that the rack causes the spur gear to rotate to expand the device. In some embodiments, the size of the spur gear is directly proportional to starting forces and expansion heights. For example, in some embodiments, larger spur gears will provide larger starting forces and expansion heights while smaller spur gears will provide smaller starting forces and expansion heights. In some embodiments, an angled pin is provided to allow sweeping expansion to accommodate a TLIF replacement.

In one embodiment, one or all of the components of the spinal implant system are disposable, peel-pack, pre-packed sterile devices used with an implant. One or all of the components of the spinal implant system may be reusable. The spinal implant system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor, infection, such as, for example, tuberculosis, and fractures. In some embodiments, the present disclosure may be employed with other osteal and bone related applications, including those associated with diagnostics and therapeutics. In some embodiments, the disclosed spinal implant system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
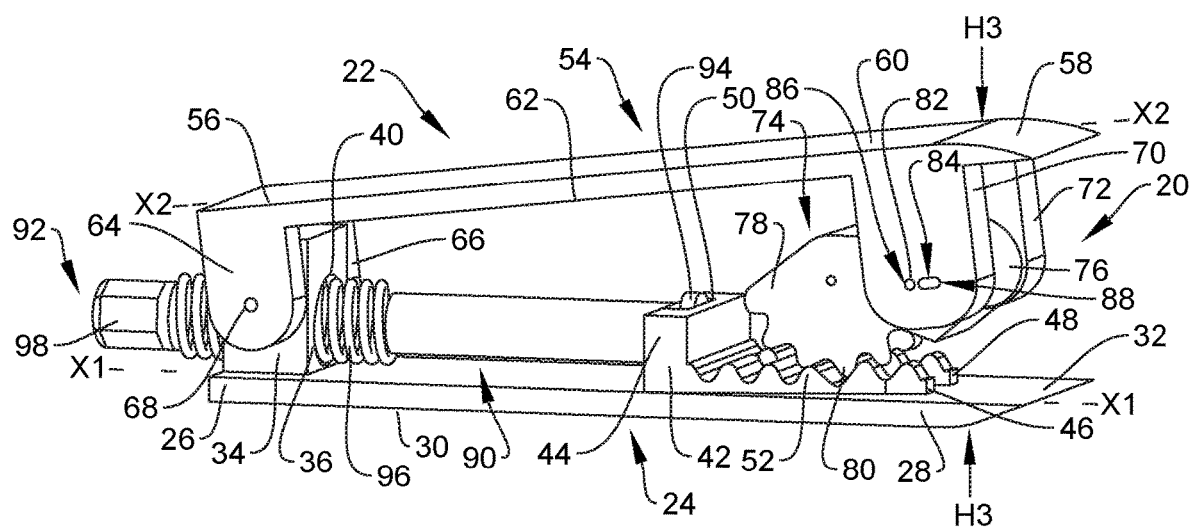
FIG. 2 is a perspective view of the implant shown in FIG. 1.
Figure 3:
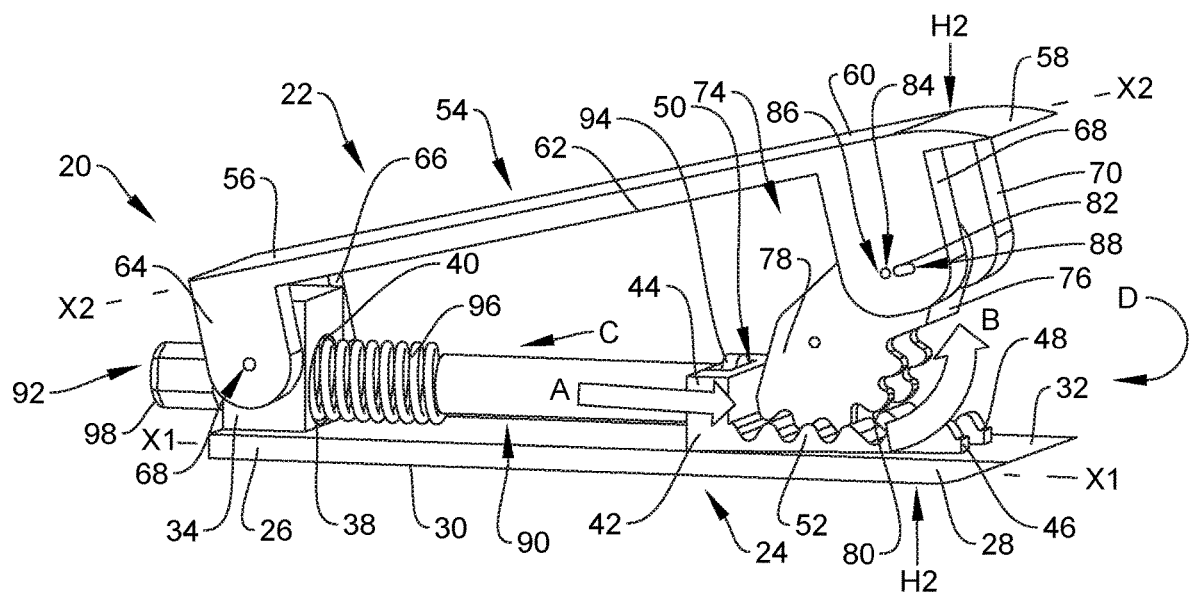
FIG. 3 is a perspective view of the implant shown in FIG. 1.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there is illustrated components of a surgical system, such as, for example, a spinal implant system 20.

The components of spinal implant system 20 can be fabricated from biologically acceptable materials suitable for medical applications, including metals, synthetic polymers, ceramics and bone material and/or their composites. For example, the components of spinal implant system 20, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 20 may have material composites, including the above materials, to achieve various desired characteristics such as strength, rigidity, elasticity, compliance, biomechanical performance, durability and radiolucency or imaging preference. The components of spinal implant system 20, individually or collectively, may also be fabricated from a heterogeneous material such as a combination of two or more of the above-described materials. The components of spinal implant system 20 may be monolithically formed, integrally connected or include fastening elements and/or instruments, as described herein.

Spinal implant system 20 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, spinal implant system 20 may be employed with surgical procedures, such as, for example, corpectomy and discectomy, which include fusion and/or fixation treatments that employ implants, to restore the mechanical support function of vertebrae.

Spinal implant system 20 includes an expandable interbody implant 22. In some embodiments, implant 22 includes a member, such as, for example, an end plate 24. Plate 24 extends along a longitudinal axis X1 between an end 26 and an opposite end 28. Plate 24 includes a vertebral engaging surface 30 and an inner surface 32 opposite surface 30. Surface 30 and/or surface 32 extend parallel to axis X1. In some embodiments, plate 24 is tapered toward end 28 to facilitate insertion of implant 22 into an intervertebral space, as discussed herein. In some embodiments, surface 30 may be rough, textured, porous, semi-porous, dimpled, knurled, toothed, grooved and/or polished to facilitate engagement with tissue. In some embodiments, surface 30 and/or surface 32 may be disposed at alternate orientations, relative to axis X1, such as, for example, transverse, perpendicular and/or other angular orientations such as acute or obtuse, co-axial and/or may be offset or staggered.

End 26 includes a block, such as, for example, an engagement portion 34 extending from surface 32. Portion 34 includes an inner surface 36 that defines a mating part, such as, for example, a female thread 38 and a passageway 40. Passageway 40 extends through an entire thickness of portion 34. Portion 34 is fixed relative to surface 32 such that portion 34 cannot move relative to surface 32. In some embodiments, portion 34 is integrally and/or monolithically formed with surface 32. In some embodiments, passageway 36 may be disposed at alternate orientations, relative to axis X1, for example, parallel, transverse, perpendicular and/or other angular orientations such as acute or obtuse, co-axial and/or may be offset or staggered. In some embodiments, portion 34 may be variously configured and dimensioned, such as, for example, square, rectangular, concave, polygonal, irregular, uniform, non-uniform, staggered, tapered, consistent or variable, depending on the requirements of a particular application.

Implant 22 includes a rack 42 movably coupled to plate 24. Rack 42 includes a body 44 and spaced apart legs 46, 48 that extend outwardly from body 44. Body 44 defines a cavity 50 configured for disposal of a component of implant 22, as discussed herein. Legs 46, 48 define a plurality of teeth 52 that extend along the entire lengths of legs 46, 48. Teeth 52 have a uniform height along the lengths of legs 46, 48. That is, crests of teeth 52 define a longitudinal axis that extends parallel to axis X1 when rack 42 is coupled to plate 24. In some embodiments, surface 32 and/or a bottom surface of rack 42 that directly engages surface 32 is smooth and/or even to allow rack 42 to slide and/or translate along surface 32, as discussed herein. In some embodiments, surface 32 is free of any recesses or projections extending into and/or from surface 32 from portion 34 to end 28. In some embodiments, the rack may be wedge shaped (the large end would have cavity 50 and the small end would be ends 46 and 48) with the teeth along the ramped face. In such embodiments, the amount of expansion of the device would be increased because since the spur gear would be rotated and translated up due to the wedge shape of 42.

A member, such as, for example, an end plate 54 extends along a longitudinal axis X2 between an end 56 and an opposite end 58. Plate 54 includes a vertebral engaging surface 60 and an inner surface 62 opposite surface 60. Surface 60 and/or surface 62 extend parallel to axis X2. In some embodiments, plate 54 is tapered toward end 58 to facilitate insertion of implant 22 into an intervertebral space, as discussed herein. In some embodiments, end 28 may meet up with end 58 to close the tip of the device for protection of the mechanism and ease-of-use during insertion. In some embodiments, surface 60 may be rough, textured, porous, semi-porous, dimpled, knurled, toothed, grooved and/or polished to facilitate engagement with tissue. In some embodiments, surface 60 and/or surface 62 may be disposed at alternate orientations, relative to axis X2, such as, for example, transverse, perpendicular and/or other angular orientations such as acute or obtuse, co-axial and/or may be offset or staggered.

End 56 includes a pair of spaced apart extensions, such as, for example, flanges 64, 66 that extend outwardly from surface 62. Portion 34 is positioned between flanges 64, 66 such that inner surfaces of flanges 64, 66 directly engage an outer surface of portion 34. Flanges 64, 66 extend perpendicular to axis X2. One or more pins, such as, for example, pin 68 extends through flange 64 and/or flange 66 and into portion 34 to couple plate 54 to plate 24 such that plate 54 is pivotable and/or rotatable relative to plate 24 about pin 68. That is, plate 54 is coupled to plate 24 such that plate 54 is rotatable relative to plate 24 about pin 68 to move implant 22 from a first orientation in which axis X2 extends parallel to axis X1, as shown in FIG. 1, to a second orientation in which axis X2 extends at an acute angle relative to axis X1, as shown in FIG. 3. Implant 22 has a maximum height H1 when implant 22 is in the first orientation, wherein the maximum height of implant 22 is defined by the distance between surface 30 and surface 60. Implant 22 has a maximum height H2 when implant 22 is in the second orientation, height H2 being greater than height H1. As implant 22 moves from the first orientation to the second orientation, implant has a maximum height H3 that is greater than height H1 and less than height H2, as shown in FIG. 2. Height H1 may be substantially the same as the height across end 56 and 26, or may be greater than or less than End 58 includes a pair of spaced apart extensions, such as, for example, arms 70, 72 that extend outwardly from surface 62. Arms 70, 72 extend parallel to axis X2. Implant 22 includes a cam, such as, for example, a spur gear 74 positioned between arms 70, 72 such that gear 74 engages rack 42. In particular, gear includes a body 76 and a portion 78 that extends from body 76. Portion 78 includes a plurality of teeth 80 that are configured to engage teeth 52 as rack 42 translates relative to plate 24 along axis X1 to move implant 22 between the first and second orientations, as discussed herein. One or more pins, such as, for example, a pin 82 extends through a slot 84 in arm 70 and/or arm 72 and into body 76 such that gear 74 is pivotable and/or rotatable relative to plate 54 and/or axis X2 about pin 82. In some embodiments, slot 84 is elongated to allow pin 82 to translate within slot 84 such that pin 82 moves between an end 86 of slot 84 and an opposite end 88 of slot 84 as implant 22 moves between the first and second orientations. In some embodiments, slot 84 extends parallel to axis X2 from end 86 to end 88. In some embodiments, slot 84 may be disposed at alternate orientations, relative to axis X2, such as, for example, transverse, perpendicular and/or other angular orientations such as acute or obtuse, and/or may be offset or staggered. In some embodiments, the interaction between the rack 42 and the spur gear 74 does not include teeth, but instead includes a generically roughened surface with no singular feature for specific engagement, such as mating gears.

Implant 22 includes a bar, such as, for example an actuator 90 including an end 92 and an opposite end 94. End 92 includes a mating part, such as, for example, a male thread 96 that engages thread 38 such that rotation of actuator 90 relative to plates 24, 54 in a first rotational direction, such as, for example, clockwise, translates rack 42 relative to plate 24 along axis X1 in the direction shown by arrow A in FIG. 3 such that gear 74 pivots relative to plate 54 in the direction shown by arrow B in FIG. 3 to move implant 22 from the first orientation, shown in FIG. 1, to the second orientation, shown in FIG. 3. Rotation of actuator 90 relative to plates 24, 54 in an opposite second rotational direction, such as, for example, counter-clockwise, translates rack 42 relative to plate 24 along axis X1 in the direction shown by arrow C in FIG. 3 such that gear 74 pivots relative to plate 54 in the direction shown by arrow D in FIG. 3 to move implant 22 from the second orientation, shown in FIG. 3, to the first orientation, shown in FIG. 1. End 92 includes a drive, such as, for example, a bit 98 configured for disposal in a socket of a driver to rotate actuator 90 relative to plates 24, 54. In some embodiments, bit 98 includes a hexalobe cross-sectional configuration configured for disposal in a socket having a hexalobe cross-sectional configuration. However, it is envisioned that bit 98 may include a square, triangular, polygonal, star cross sectional configuration configured engage a correspondingly shaped socket of a driver.

End 94 directly engages rack 42 for disposal of end 94 in cavity 50 to couple actuator 90 to rack 42 such that actuator 90 is rotatable relative to rack 42 and translation of actuator 90 relative to plates 24, 54 along axis X1 also translates rack 42 relative to plates 24, 54 along axis X1. In some embodiments, end 94 can be variously connected with rack 42, such as, for example, frictional engagement, threaded engagement, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts.

In assembly, operation and use, spinal implant system 20, similar to the systems and methods described herein, and including implant 22 is employed with a surgical procedure, such as, for example, a lumbar corpectomy for treatment of a spine of a patient including vertebrae. Spinal implant system 20 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including vertebral replacement devices, interbody devices, plates, rods, and bone engaging fasteners for securement of the components of implant 22.

Spinal implant system 20 is employed with a lumbar corpectomy including surgical arthrodesis, such as, for example, fusion to immobilize a joint for treatment of an applicable condition or injury of an affected section of a spinal column and adjacent areas within a body. In some embodiments, implant 22 is configured for insertion within a vertebral space to space apart articular joint surfaces, provide support and maximize stabilization of vertebrae.

In use, to treat the affected section of vertebrae, a medical practitioner obtains access to a surgical site including vertebrae in any appropriate manner, such as through incision and retraction of tissues. In some embodiments, spinal implant system 20 may be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, corpectomy is performed for treating the spine disorder. The diseased and/or damaged portion of vertebrae, and diseased and/or damaged intervertebral discs are removed to create a vertebral space.

A preparation instrument is employed to remove disc tissue, fluids, adjacent tissues and/or bone, and scrape and/or remove tissue from a vertebral surface of a superior vertebra and/or a vertebral surface of an inferior vertebra. Implant 22 may be provided with at least one agent, similar to those described herein, to promote new bone growth and fusion to treat the affected section of vertebrae. The components of spinal implant system 20 may be completely or partially revised, removed or replaced. In some embodiments, implant 22 is employed to stabilize vertebrae as a pre-assembled device or can be assembled in situ.

Implant 22 is inserted into a vertebral space via a posterior approach, with implant 22 in the first orientation, as shown in FIG. 1. A driver is coupled to bit by inserting bit 98 into a socket of the driver. The driver rotates actuator 90 to move implant 22 from the first orientation, shown in FIG. 1, to the second orientation, as shown in FIG. 3.

In some embodiments, implant 22 may be moved from the first orientation to the second orientation until surface 30 directly engages an end plate of a superior vertebra and surface 60 directly engages an end plate of an inferior vertebra. In some embodiments, a material, such as, for example, bone graft material is inserted through into implant 22.

In some embodiments, implant 22 may include fastening elements, which may include locking structure, configured for fixation with vertebrae to secure joint surfaces and provide complementary stabilization and immobilization to a vertebral region. In some embodiments, locking structure may include fastening elements such as, for example, rods, plates, clips, hooks, adhesives and/or flanges. In some embodiments, spinal implant system 20 can be used with screws to enhance fixation. In some embodiments, spinal implant system 20 and any screws and attachments may be coated with an agent, similar to those described herein, for enhanced bony fixation to a treated area. The components of spinal implant system 20 can be made of radiolucent materials such as polymers. Radiomarkers may be included for identification under x-ray, fluoroscopy, CT or other imaging techniques.

In some embodiments, the height of implant 22 may be decreased by coupling the driver to implant 22, as discussed herein, and rotating the driver to move implant from the second orientation, shown in FIG. 3, to the first orientation, shown in FIG. 1. Pin 82 allows the device to pull itself closed and not disarticulate.

In some embodiments, the use of microsurgical and image guided technologies may be employed to access, view and repair spinal deterioration or damage, with the aid of spinal implant system 20. Upon completion of the procedure, the non-implanted components, surgical instruments and assemblies of spinal implant system 20 are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

In the figures, the implant shown has one spur gear and one rack for pushing it. Two, opposing spurs and a common rack for driving them is conceived such that twice the expansion could be achieved for the same amount of actuation.

Such a rack and pinion type activation/expansion mechanism could be used within a motion sparing device to change its firmness. In a specific example, if the disclosed device was surrounded in flexible materials then placed in the disc space, as the internal device is expanded, the soft material trapped between each endplate (24 and 54) would be compressed and the stiffness of those would increase. For more motion desired, less expansion would be needed, therefore less stiffness, and vise versa.

What is claimed is:

1. A spinal implant comprising:
a first member extending along a first longitudinal axis between opposite first and second ends, the first end comprising a first mating part;
a rack coupled to the first member;
a second member extending along a second longitudinal axis between opposite first and second ends;
a gear coupled to the second end of the second member such that the gear engages the rack; and
an actuator comprising a second mating part that engages the first mating part such that rotation of the actuator relative to the first and second members translates the rack relative to the first member along the first longitudinal axis to move the implant between a first orientation in which the second longitudinal axis extends parallel to the first longitudinal axis and a second orientation in which the second longitudinal axis extends at an acute angle relative to the first longitudinal axis,
wherein the first mating part is a female thread and the second mating part is a male thread.

2. The spinal implant recited in claim 1, wherein:
the first member comprises a first vertebral engaging surface and the second member comprises an opposite second vertebral engaging surface, a distance between the first and second vertebral engaging surfaces defining a maximum height of the implant; and
wherein the maximum height of the implant is greater when the implant is in the second orientation than when the implant is in the first orientation.

3. The spinal implant recited in claim 1, wherein the rack includes first teeth and the gear includes second teeth, the second teeth engaging the first teeth as the implant moves between the first and second orientations.

4. The spinal implant recited in claim 1, wherein the rack includes arms each having first teeth and the gear includes legs each having of second teeth, the second teeth engaging the first teeth as the implant moves between the first and second orientations.

5. The spinal implant recited in claim 1, wherein the gear rotates relative to the second member as the implant moves between the first and second orientations.

6. The spinal implant recited in claim 1, further comprising a pin extending into the first end of the first member and the first end of the second member such that the second member is pivotable relative to the first member about the pin.

7. The spinal implant recited in claim 1, wherein the actuator is rotatably coupled to the rack.

8. The spinal implant recited in claim 1, wherein the actuator comprises a first end that includes the second mating part and an opposite second end, the second end of the actuator directly engaging the rack.

9. A spinal implant comprising:
a first member including a first vertebral engaging surface, the first member extending along a first longitudinal axis between opposite first and second ends, the first end comprising a first mating part;
a rack coupled to the first member;
a second member including a second vertebral engaging surface, the second member extending along a second longitudinal axis between opposite first and second ends;
a gear coupled to the second end of the second member; and
an actuator comprising a second mating part that engages the first mating part,
wherein a distance between the first and second vertebral engaging surfaces defines a height of the implant,
wherein rotation of the actuator relative to the first and second members translates the rack relative to the first member along the first longitudinal axis such that the gear rotates relative to the rack to increase the height of the implant, and
wherein the first mating part is a female thread and the second mating part is a male thread.

10. The spinal implant recited in claim 9, wherein rotation of the actuator relative to the first and second members translates the rack along the first longitudinal axis to move the implant between a first orientation in which the second longitudinal axis extends parallel to the first longitudinal axis and a second orientation in which the second longitudinal axis extends at an acute angle relative to the first longitudinal axis.

11. The spinal implant recited in claim 9, wherein the rack includes first teeth and the gear includes a second teeth, the second teeth engaging the first teeth as the rack translates relative to the first member along the first longitudinal axis.

12. The spinal implant recited in claim 9, wherein the rack includes arms each having first teeth and the gear includes legs each having second teeth, the second teeth engaging the first teeth as the rack translates relative to the first member along the first longitudinal axis.

13. The spinal implant recited in claim 9, wherein the gear rotates relative to the second member as the rack translates relative to the first member along the first longitudinal axis.

14. The spinal implant recited in claim 9, further comprising a pin extending into the first end of the first member and the first end of the second member such that the second member is pivotable relative to the first member about the pin.

15. The spinal implant recited in claim 9, wherein the actuator is rotatably coupled to the rack.

16. The spinal implant recited in claim 9, wherein the actuator comprises a first end that includes the second mating part and an opposite second end, the second end of the actuator directly engaging the rack.

17. The spinal implant recited in claim 9, wherein the second end of the second member comprises extensions, the gear being positioned between the extensions such that a pin extends through the extensions and the gear, and wherein the gear is pivotable relative to the extensions about the pin.

18. A spinal implant comprising: a first member including a first vertebral engaging surface, the first member extending along a first longitudinal axis between opposite first and second ends, the first end comprising a first mating part; a rack coupled to the first member; a second member including a second vertebral engaging surface, the second member extending along a second longitudinal axis between opposite first and second ends; a gear coupled to the second end of the second member; and an actuator comprising a second mating part that engages the first mating part, wherein a distance between the first and second vertebral engaging surfaces defines a height of the implant, wherein rotation of the actuator relative to the first and second members translates the rack relative to the first member along the first longitudinal axis such that the gear rotates relative to the rack to increase the height of the implant, and wherein the second end of the second member comprises extensions, the gear being positioned between the extensions such that a pin extends through the extensions and the gear, and wherein the gear is pivotable relative to the extensions about the pin.

19. The spinal implant recited in claim 18, wherein rotation of the actuator relative to the first and second members translates the rack along the first longitudinal axis to move the implant between a first orientation in which the second longitudinal axis extends parallel to the first longitudinal axis and a second orientation in which the second longitudinal axis extends at an acute angle relative to the first longitudinal axis.

20. The spinal implant recited in claim 18, wherein the rack includes first teeth and the gear includes second teeth, the second teeth engaging the first teeth as the rack translates relative to the first member along the first longitudinal axis.

* * * * *

UNITED STATES PATENT AND TRADEMARK OFFICE
CERTIFICATE OF CORRECTION

PATENT NO. : 11,344,429 B2
APPLICATION NO. : 16/867216
DATED : May 31, 2022
INVENTOR(S) : Jonathan M. Dewey It is certified that error appears in the above-identified patent and that said Letters Patent is hereby corrected as shown below:

In the Claims

Column 10, Line 1, delete "of".

Signed and Sealed this
Sixteenth Day of August, 2022

*Katherine Kelly Vidal*

Katherine Kelly Vidal
*Director of the United States Patent and Trademark Office*